(12) United States Patent
Irie

(10) Patent No.: US 8,875,415 B2
(45) Date of Patent: Nov. 4, 2014

(54) METHOD FOR DRYING GRANULAR WATER-CONTAINING GEL-LIKE CROSS-LINKED POLYMER

(75) Inventor: Yoshio Irie, Himeji (JP)

(73) Assignee: Nippon Shokubai, Co., Ltd., Osaka (JP)

( * ) Notice: Subject to any disclaimer, the term of this patent is extended or adjusted under 35 U.S.C. 154(b) by 176 days.

(21) Appl. No.: 13/583,144

(22) PCT Filed: Mar. 7, 2011

(86) PCT No.: PCT/JP2011/055250
§ 371 (c)(1),
(2), (4) Date: Sep. 6, 2012

(87) PCT Pub. No.: WO2011/111657
PCT Pub. Date: Sep. 15, 2011

(65) Prior Publication Data
US 2012/0329953 A1 Dec. 27, 2012

(30) Foreign Application Priority Data

Mar. 8, 2010 (JP) ................................. 2010-050710

(51) Int. Cl.
| | | |
|---|---|---|
| C08F 6/06 | (2006.01) | |
| C08F 6/00 | (2006.01) | |
| B01J 2/26 | (2006.01) | |
| C08L 33/02 | (2006.01) | |
| C08F 22/02 | (2006.01) | |
| B01D 1/24 | (2006.01) | |
| A61L 15/22 | (2006.01) | |
| A61L 15/60 | (2006.01) | |
| C08J 3/12 | (2006.01) | |

(52) U.S. Cl.
CPC . *C08F 6/008* (2013.01); *B01J 2/26* (2013.01); *C08L 33/02* (2013.01); *C08F 22/02* (2013.01); *B01D 1/24* (2013.01); *A61L 15/22* (2013.01); *A61L 15/60* (2013.01); *C08J 3/12* (2013.01); C08J 2300/14 (2013.01)
USPC ............... 34/507; 34/452; 264/486; 264/344; 502/402; 523/331; 526/317.1

(58) Field of Classification Search
None
See application file for complete search history.

(56) References Cited

U.S. PATENT DOCUMENTS

| | | | |
|---|---|---|---|
| 2,397,350 A * | 3/1946 | Daley et al. ........................ 502/8 |
| 4,920,202 A | 4/1990 | Irie et al. | |
| 5,250,640 A | 10/1993 | Irie et al. | |
| 5,275,773 A | 1/1994 | Irie et al. | |
| 6,187,902 B1 | 2/2001 | Yanase et al. | |
| 6,207,796 B1 | 3/2001 | Dairoku et al. | |
| 2001/0025093 A1 * | 9/2001 | Ishizaki et al. ................ 526/210 |
| 2004/0110897 A1 * | 6/2004 | Sakamoto et al. ............ 524/832 |
| 2008/0119626 A1 * | 5/2008 | Fujimaru et al. ........... 526/317.1 |
| 2008/0161512 A1 | 7/2008 | Kawano et al. | |
| 2008/0214749 A1 * | 9/2008 | Weismantel et al. ........... 526/73 |
| 2010/0016522 A1 | 1/2010 | Stueven et al. | |
| 2011/0028670 A1 | 2/2011 | Matsumoto et al. | |
| 2011/0088806 A1 | 4/2011 | Nogi et al. | |
| 2011/0110703 A1 | 5/2011 | Cheng et al. | |

FOREIGN PATENT DOCUMENTS

| | | |
|---|---|---|
| EP | A-574248 | 12/1993 |
| JP | A-64-026604 | 1/1989 |
| JP | A-5-070597 | 3/1993 |
| JP | A-5-112654 | 5/1993 |
| JP | A-5-247225 | 9/1993 |
| JP | A-5-339381 | 12/1993 |
| JP | A-6-041319 | 2/1994 |
| JP | B-3297192 | 10/1995 |
| JP | B-2700531 | 3/1996 |
| JP | A-11-240914 | 9/1999 |
| JP | A-2008-534695 | 8/2008 |
| WO | WO 2008/037676 | 4/2008 |
| WO | WO 2009/119754 | 10/2009 |

OTHER PUBLICATIONS

The Modern Superabsorbent Polymer Technology (1998), p. 87 to 93.

* cited by examiner

*Primary Examiner* — Robert C Boyle
(74) *Attorney, Agent, or Firm* — Cesari and McKenna, LLP

(57) ABSTRACT

The present invention is to provide a drying method by which both cost reduction and superior physical properties can be attained in a step which comprises subjecting a water-containing gel-like crosslinked polymer obtained by polymerizing an aqueous monomer solution to fine granulation during or after the polymerization, and drying the resultant particulate water-containing gel-like crosslinked polymer with a through-circulation band dryer. The method has a feature in that the drying conditions over a period from a time of introducing the particulate water-containing gel-like crosslinked polymer into a drying zone of the through-circulation band dryer to a time of reaching a solid content concentration thereof to 80% by weight, satisfy that (1) a difference of temperature between a temperature of hot air blown to a particulate hydrogel layer and a temperature measured after the hot air passes through the particulate hydrogel layer is 20 to 70° C.

13 Claims, 1 Drawing Sheet

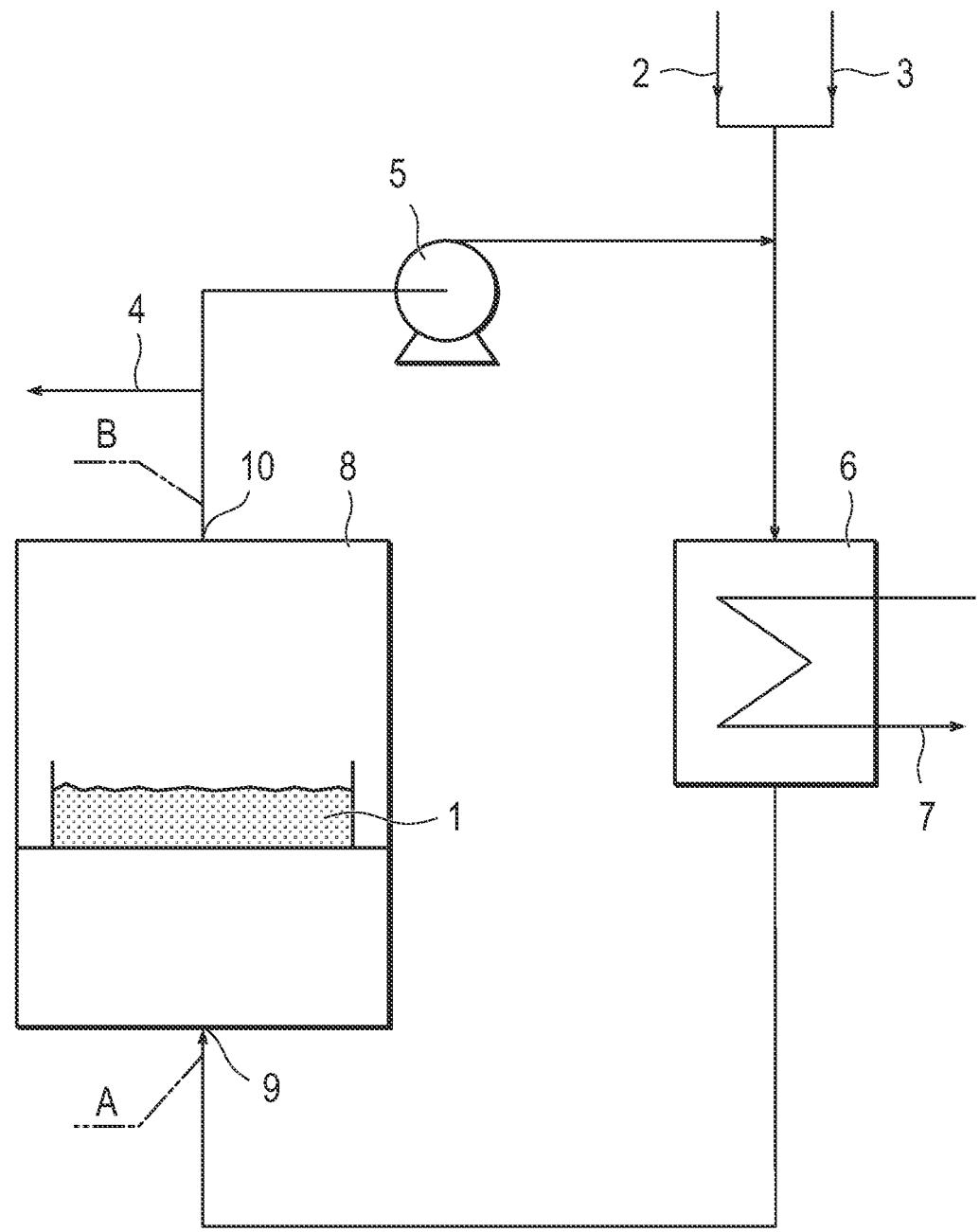

METHOD FOR DRYING GRANULAR WATER-CONTAINING GEL-LIKE CROSS-LINKED POLYMER

CROSS REFERENCE TO RELATED APPLICATIONS

This application is a National Stage of International Application No. PCT/JP2011/055250 filed on Mar. 7, 2011, which claims priority to Japanese Application No. 2010-050710 filed Mar. 8, 2010. The contents of the prior applications are incorporated herein by reference in their entirety.

TECHNICAL FIELD

The present invention relates to a method for drying a particulate water-containing gel-like crosslinked polymer in a step for producing a water absorbent resin.

BACKGROUND ART

A water absorbent resin (alternately referred to as "water absorbent polymer, SAP/Super Absorbent Polymer") is a water-swellable, water-insoluble polymer gelling agent, and has been frequently used primarily in disposable applications as water absorbent articles such as paper diapers and sanitary napkins, as well as water retention agents for agricultural and horticultural use, industrial water stopping materials, and the like. As such a water absorbent resin, many monomers and hydrophilic polymers have been proposed as a raw material. Among others, a polyacrylic acid (salt)-type water absorbent resin which uses acrylic acid and/or salts thereof as a monomer has been industrially most frequently used due to its high water absorption performance.

Such a water absorbent resin is obtained by polymerizing an aqueous monomer solution to obtain a water-containing gel-like crosslinked polymer, subjecting the water-containing gel-like crosslinked polymer to fine granulation during or after the polymerization, drying the resultant particulate water-containing gel-like crosslinked polymer, and subjecting the dried polymer to steps such as pulverization, classification, and surface crosslinking. As an apparatus for drying the particulate water-containing gel-like crosslinked polymer, a through-circulation band dryer or the like can be used (Non-Patent Literature 1).

For drying conditions of a particulate water-containing gel-like crosslinked polymer, various methods have been proposed for enhancement of physical properties of a water absorbent resin to be obtained (for example, reduction in residual monomers, enhancement of absorption capacity, and reduction in extractables, and the like). Specifically, for the purpose of reducing residual monomers, a method of controlling a dew point or temperature in an atmosphere inside a dryer (Patent Literature 1) has been proposed, and for the purpose of repressing changes in physical properties as a result of drying, a method of using, at the time of drying a water-containing gel-like crosslinked polymer with a through-circulation band dryer, an upward warm air for former half part in drying step and a downward warm air for latter half part in the drying step, and drying the polymer with a gas at a predetermined rate (Patent Literature 2) has been proposed.

In a method of drying a water-containing gel-like crosslinked polymer with a band dryer, a method of measuring a difference between a pressure on a side where hot air is blown to a hydrogel polymer layer and a pressure on the opposite side thereof, in order not to produce any undried product (Patent Literature 3), and a method for drying hydrogel polymer, which for the purpose of uniform drying, comprises setting a roll having plural pins protruded on the peripheral surface and having a rotation axis perpendicular to a conveyance direction of a conveyor on the conveyor at conveyance initiation point, starting operation of the conveyor, placing a hydrogel polymer in front of the roll and passing the polymer between the roll and the conveyor at the initiation of conveyance while the roll is rotated, prior to drying the polymer (Patent Literature 4) have been known. A drying method which comprises, in drying a hydrogel polymer, drying the hydrogel polymer until a moisture content thereof reaches within a specific range, maintaining the same conditions for 10 minutes or more, and then carrying out finish drying (Patent Literature 5) has been also known. Further, a drying method which comprises controlling drive of a continuous belt type dryer by continuously measuring a moisture content of a hydrogel polymer during or after drying (Patent Literature 6) has been known.

PRIOR ART DOCUMENTS

Patent Literature

Patent Literature 1: U.S. Pat. No. 4,920,202
Patent Literature 2: US Publication No. 2008/0,214,749
Patent Literature 3: JP Patent No. 2700531
Patent Literature 4: JP Patent No. 3297192
Patent Literature 5: U.S. Pat. No. 6,207,796
Patent Literature 6: WO 2008/037676

Non-Patent Literature

Non-Patent Literature 1: Modern Superabsorbent Polymer Technology (1998) p. 87-93

SUMMARY OF INVENTION

In recent years, due to the attempts to reduce a thickness of paper diapers, and due to the tendency for increase in an amount of used water absorbent resin per sheet of a paper diaper, manufacturers of water absorbent resins are under the pressure of cost reduction. Accordingly, increase in a polymerization concentration (increase in a concentration of aqueous monomer solution) has been promoted, along with a scale-up of production apparatus. On the other hand, there has been a demand for a water absorbent resin having higher performance than that of conventional resins, for the applications of thin paper diapers. Specifically, there is a demand for a water absorbent resin which is further superior in terms of absorption capacity without load and under load, liquid permeability between gel particles, absorption rate, residual monomers, and the like.

A thorough investigation was conducted in order to solve a difficult problem of achieving both low cost and superior physical properties in a step of polymerizing an aqueous monomer solution to obtain a water-containing gel-like crosslinked polymer (hereinafter, referred to as "hydrogel"), subjecting the water-containing gel-like crosslinked polymer to fine granulation during or after the polymerization, and drying the resultant particulate water-containing gel-like crosslinked polymer in a through-circulation band dryer, to be found that the above problem can be solved under specific drying conditions.

Specifically, it is contemplated that in the step for drying a particulate water-containing gel-like crosslinked polymer according to this invention, not only the moisture contained in the particulate water-containing gel-like crosslinked polymer is evaporated, but also, at least one of the chemical reactions listed below occurs simultaneously with the drying of the particulate water-containing gel-like crosslinked polymer.
1. Progress of polymerization
(A) Radical generation due to decomposition of a polymerization initiator
(B) Radical addition polymerization
2. Degradation/deterioration of polymer
(A) Degradation of polymer main chain
(B) Degradation of crosslinked part
(C) Coloration due to oxidation
3. Crosslinking between polymers To be specific, since it is believed that these chemical reactions would occur depending on drying conditions, they would have effects on characteristics of the resultant water absorbent resin. Therefore, a thorough investigation was conducted in order to satisfy both high-level characteristics of a water absorbent resin and economic efficiency, and as a result, the following finding has been finally obtained.

The method for drying a particulate water-containing gel-like crosslinked polymer of this invention is method for drying a particulate water-containing gel-like crosslinked polymer which has a feature in carrying our initial drying under specific conditions in drying with a through-circulation dryer, after polymerizing acrylic acid (or partially neutralized salt thereof) with a crosslinking agent in an aqueous solution containing acrylic acid (or salt thereof) as a main component to obtain a hydrogel of a partially neutralized salt of polyacrylic acid, coarse crushing the hydrogel, and drying it with through-circulation dryer.

Specifically, there is provided a method for drying a particulate water-containing gel-like crosslinked polymer which comprises polymerizing acrylic acid (or partially neutralized salt thereof) with a crosslinking agent in an aqueous solution to obtain a particulate water-containing gel-like crosslinked polymer of a partially neutralized salt of polyacrylic acid and having a solid content concentration of 35% to 75% by weight, and drying the particulate water-containing gel-like crosslinked polymer with a through-circulation dryer using hot air having a temperature of 130 to 230° C. and a dew point of 50 to 80° C., wherein over 60% or more of a period from a time of introducing the particulate water-containing gel-like crosslinked polymer into a drying zone of the through-circulation dryer to a time of reaching a solid content concentration thereof to 80% by weight, a difference of temperature ($\Delta T$) between a temperature of hot air blown to a particulate hydrogel layer and a temperature measured after the hot air passes through the particulate hydrogel layer is 20 to 70° C.

Meanwhile, since the particulate water-containing gel-like crosslinked polymer introduced into the drying step of this invention has a decreased water content with the progress of the drying step, the moisture content thereof would reach several percent (%) by weight. Eventually, the particulate water-containing gel-like crosslinked polymer may be in a state which substantially may not be called "water-containing." However, in the present specification, until the particulate water-containing gel-like crosslinked polymer that has been introduced into the drying step is discharged from the dryer, the polymer will be referred to as "particulate water-containing gel-like crosslinked polymer" for convenience, irrespective of the transition and change of moisture content.

By drying a particulate water-containing gel-like crosslinked polymer under the drying conditions defined in this invention, a water absorbent resin having superior physical properties can be obtained at low cost.

BRIEF DESCRIPTION OF DRAWINGS

FIG. 1 is a schematic flow diagram of a through-circulation dryer used in the Examples of this invention. In FIG. 1, reference numeral 1 represents a particulate water-containing gel-like crosslinked polymer; 2 represents a fresh air inlet tube; 3 represents a water vapor inlet tube; 4 represents a discharge pipe; 5 represents a blower; 6 represents a heat exchanger; 7 represents a heat medium inlet tube; 8 represents a hot air dryer (through-circulation dryer); 9 represents a hot air inlet; and 10 represents a hot air outlet.

DESCRIPTION OF EMBODIMENTS

Hereinafter, the method for producing a water absorbent resin according to this invention will be described in detail. However, the scope of this invention is not intended to be restrained by these descriptions, and this invention can be appropriately modified and carried out for embodiments other than the following examples without departing from the scope of this invention. Specifically, this invention is not intended to be limited to the various embodiments described below, and can be modified variously within the scope defined by the claims. Embodiments having appropriately combined technical means respectively disclosed in different embodiments, can also be included in the technical scope of this invention.

[1] Definition of Term (1-1) "Water Absorbent Resin"

As used herein, the term "water absorbent resin" is referred to as a water-swelling and water-insoluble polymer gelling agent. As used herein, the term "water-swellable" means that CRC (absorption capacity without load) specified in ERT441.2-02 is essentially 5 [g/g] or higher, preferably 10 to 100 [g/g], and still more preferably 20 to 80 [g/g]. The term "water-insoluble" means that Ext (Extractables) specified in ERT470.2-02 is essentially 0% to 50% by weight, preferably 0% to 30% by weight, still more preferably 0% to 20% by weight, and particularly preferably 0% to 10% by weight.

The water absorbent resin can be appropriately designed in accordance with its application, and is not particularly limited. The water absorbent resin is preferably a hydrophilic crosslinked polymer obtained by cross-linking polymerization of an unsaturated monomer having a carboxyl group. The water-absorbent resin is not limited to a form where whole amount (100% by weight) is a polymer, and may include an additive which is described later or the like in a range to maintain the performance. Specifically, even a water-absorbent resin composition is called generically a water-absorbent resin in the present invention. A content of a polyacrylic acid (salt)-type water-absorbent resin is preferably 70 to 99.9% by weight, more preferably 80 to 99.7% by weight, and still more preferably 90 to 99.5% by weight, relative to total amount. As components other than the water-absorbent resin, in view of water absorbing speed or impact resistance of powders (particles), water is preferable, and an additive to be described later may be contained, as needed.

(1-2) "Polyacrylic Acid (Salt)"

In the present description, the "polyacrylic acid (salt)" is referred to as a polymer containing an arbitrary graft component, and having as a main component acrylic acid and/or a salt thereof (hereinafter, referred to as acrylic acid (salt)) as a repeating unit.

Specifically, it contains acrylic acid (salt) essentially in 50 to 100% by mole, preferably 70 to 100% by mole, more preferably 90 to 100% by mole, particularly preferably substantially 100% by mole, as a monomer used in the polymerization (excluding a cross-linking agent). The salt as the polymer contains essentially a water-soluble salt, which is preferably a monovalent salt, still more preferably an alkali metal salt or an ammonium salt, particularly an alkali metal salt, and further a sodium salt.

(1-3) "EDANA" and "ERT"

"EDANA" is an abbreviation of European Disposables and Nonwovens Association, and "ERT" is an abbreviation of measurement method for a water-absorbent resin of an European standard (nearly a world standard) (EDANA Recommended Test Method).

In the present description, unless otherwise specified, physical properties of a water-absorbent resin are measured based on the ERT original (known document: revised in 2002).

(a) "CRC" (ERT441.2-02)

"CRC" is an abbreviation of Centrifuge Retention Capacity, and means absorption capacity without load (it may also be referred to simply "absorption capacity"). Specifically, it is absorption capacity (unit; g/g) after immersing 0.200 g of a water-absorbent resin in a non-woven bag in an excess amount of an aqueous 0.9% by weight sodium chloride solution for 30 minutes, and then draining water therefrom with a centrifugal separating machine.

(b) "AAP" (ERT442.2-02)

AAP is an abbreviation of Absorption Against Pressure, and means absorption capacity under load. Specifically, it means absorption capacity (unit; g/g) after swelling 0.900 g of a water-absorbent resin with an excess amount of an aqueous 0.9% by weight sodium chloride solution under a load of 2.06 kPa (0.3 psi, 21 [g/cm$^2$]) for 1 hour. It should be noted that in the present invention, it was measured by changing the load conditions to 4.83 kPa (0.7 psi, 50 [g/cm$^2$]).

(c) "Ext" (ERT470.2-02)

"Ext" is an abbreviation of Extractables, and means a water-soluble content (amount of water-solubles). Specifically, it is a value (unit; % by weight) obtained by stirring 1 g of a water-absorbent resin in 200 g of an aqueous 0.9% by weight sodium chloride solution for 16 hours, and measuring an amount of dissolved polymer by pH titration.

(d) "Residual Monomers" (ERT410.2-02)

"Residual Monomers" mean an amount of monomer (s) remaining in a water-absorbent resin. Specifically, it is a value (unit; ppm by weight) obtained by charging 1.0 g of a water-absorbent resin into 200 mL of an aqueous 0.9% by weight sodium chloride solution, stirring the mixture for 2 hours, and measuring an amount of eluted monomer(s) into the aqueous solution by high-performance liquid chromatography.

(e) "PSD" (ERT420.2-02)

"PSD" is an abbreviation for Particle Size Distribution, and means a particle size distribution measured by sieve classification. A weight average particle diameter (D50) and a particle size distribution width are measured by a method similar to "(1) Average Particle Diameter and Distribution of Particle Diameter" described in EP 0 349 240 B, page 7, lines 25-43.

(f) Others, Physical Properties of Water Absorbent Resin Defined by EDANA

"pH" (ERT400.2-02): it means pH of a water absorbent resin.

"Moisture Content" (ERT430.2-02): it means a water content of a water absorbent resin.

"Flow Rate" (ERT450.2-02): it means a flow-down speed of a water absorbent resin.

"Density" (ERT460.2-02): it means a bulk specific gravity of a water absorbent resin.

"Respirable Particles" (ERT480.2-02): it means a inhalable particles of a water absorbent resin.

"Dust" (ERT490.2-02): it means a dust contained in a water absorbent resin.

(1-4) "Liquid Permeability"

In the present description, "liquid permeability" means fluid flow among swollen gel particles under load or without load. As a typical evaluation method thereof, there is an evaluation method of SFC (Saline Flow Conductivity) and GBP (Gel Bed Permeability).

"SFC (saline flow conductivity)" is liquid permeability of an aqueous 0.69% by weight sodium chloride solution for 0.9 g of a water absorbent resin under load of 0.3 psi. It is measured in accordance with SFC test described in U.S. Pat. No. 5,669,894.

"GBP" indicates liquid permeability of a 0.69% by weight physiological saline for a water absorbent resin under load or in free expansion. It is measured in accordance with GBP test described in WO 2005/016393 pamphlet.

(1-5) Others

In the present description, "X to Y" showing a range indicates to be equal to or higher than X and equal to or lower than Y. Also, "t (ton)" as a unit of weight means "Metric Ton". Unless otherwise specified, "ppm" should mean "ppm by weight" or "ppm by mass". In the present description, "mass", "% by mass" and "parts by mass" are used synonymously to "weight", "% by weight" and "parts by weight", respectively. Still more, physical properties or the like is measured at room temperature (20 to 25° C.)/a relative humidity of 40 to 50%, unless otherwise specified. Furthermore, the term " . . . acid (salt)" means " . . . acid and/or salt thereof", and "(meth)acrylic" means "acrylic and/or methacrylic".

[2] Method for Producing Water Absorbent Resin (2-1) Polymerization Step

The present step is a step of polymerizing an aqueous solution containing acrylic acid and/or a salt thereof as a main component (hereinafter, referred to as "acrylic acid (salt)") and thereby obtaining a water-containing gel-like crosslinked polymer.

(a) Monomer (Excluding a Cross-Linking Agent)

The water-absorbing resin obtained in this invention uses as a raw material (monomer) thereof an aqueous solution containing acrylic acid (salt) as a main component, and is generally polymerized in a state of an aqueous solution. A monomer concentration (solid content concentration) in the aqueous monomer solution is usually 10% to 90% by weight, preferably 20% to 80% by weight, more preferably 30% to 70% by weight, and still more preferably 40% to 60% by weight. Further, when a monomer is polymerized in an aqueous solution, a surfactant, a polymer compound such as polyacrylic acid (salt), starch, cellulose, and polyvinyl alcohol, various chelating agents, and various additives may be added as necessary, in an amount of 0% to 30% by weight, and preferably 0.001% to 20% by weight, relative to the monomer(s).

Furthermore, the hydrogel obtainable by polymerization of the aqueous solution has at least a portion of the acid groups of the polymer neutralized, from the viewpoint of water absorption performance. The neutralization can be carried out before polymerization, during polymerization, or after polymerization of acrylic acid, but from the viewpoints of productivity of a water absorbent resin, and an enhancement of AAP (absorbency against pressure) or SFC (saline flow conductivity) of the water absorbent resin, it is preferable to carry out neutralization before the polymerization of acrylic acid. Specifically, it is preferable to use neutralized acrylic acid (that is, a partially neutralized salt of acrylic acid) as a monomer.

A neutralization ratio of acrylic acid (salt) or preferably a water absorbent resin thus obtainable is not particularly limited. The neutralization ratio is preferably 10% to 100% by mole (preferably, less than 100%), more preferably 30% to 95% by mole, still more preferably 50% to 90% by mole, and particularly preferably 60% to 80% by mole, relative to the acid group. If the neutralization ratio is less than 10% by mole, CRC (absorption capacity without load) in particular may be markedly decreased, which would not be preferable. The neutralization may also be carried out after polymerization by using an aqueous solution containing unneutralized or partially neutralized acrylic acid (salt) as a main component, but preferably, acrylic acid is neutralized as a monomer.

In the case of using acrylic acid (salt) as a main component in this invention, a hydrophilic or hydrophobic unsaturated monomer (hereinafter, also referred to as "another monomer") other than acrylic acid (salt) can also be used. There are no particular limitations on such another monomer. Examples thereof may include methacrylic acid, (anhydrous) maleic acid, 2-(meth)acrylamido-2-methylpropanesulfonic acid, (meth)acryloxyalkanesulfonic acid, N-vinyl-2-pyrrolidone, N-vinylacetamide, (meth)acrylamide, N-isopropyl (meth)acrylamide, N,N-dimethyl (meth)acrylamide, 2-hydroxyethyl (meth)acrylate, methoxypolyethylene glycol(meth)acrylate, polyethylene glycol(meth)acrylate, stearyl acrylate, and salts thereof. When these other monomers are used, the amount thereof to be used is not particularly limited as long as it does not impair absorption properties of the resultant water absorbent resin. It is preferably 50% by weight or less, and more preferably 20% by weight or less, relative to the total weight of monomers. Also, in the case of using the another monomer that is used as necessary, the lower limit of the amount can be appropriately determined in accordance with the kind, purpose, or effect thereof, and is not particularly limited. It is about 1% by weight relative to the total weight of monomers.

(b) Salt of Neutralization

There are no particular limitations on a basic substance used in the neutralization of acrylic acid as the monomer or a polymer (hydrogel) after polymerization, but a monovalent basic substance including hydroxides of alkali metal such as sodium hydroxide, potassium hydroxide, and lithium hydroxide, and (hydrogen) carbonates such as sodium (hydrogen) carbonate and potassium (hydrogen) carbonate are preferred, and sodium hydroxide is particularly preferred. A temperature in the neutralization (neutralization temperature) is not particularly limited, and the temperature is preferably 10° C. to 100° C., and more preferably 30° C. to 90° C. In regard to neutralization treatment conditions and the like other than those described above, conditions disclosed in WO 2004/085496 A and the like are preferably applied to this invention.

(c) Crosslinking Agent (Internal Crosslinking Agent)

In this invention, a crosslinking agent (hereinafter, also referred to as "internal crosslinking agent") may be used from the viewpoint of water absorption performance of the water absorbent resin to be obtained. Examples of the internal crosslinking agent that can be used include compounds having two or more polymerizable double bonds per molecule, and polyfunctional compounds having two or more functional groups per molecule capable of reacting with a carboxyl group to form a covalent bond. For example, one or more of polymerizable crosslinking agents capable of polymerizing with acrylic acid, reactive crosslinking agents capable of reacting with a carboxyl group, and crosslinking agents capable of polymerizing with acrylic acid and reacting with a carboxyl group, may be cited. Specifically, as the polymerizable crosslinking agent, for example, compounds having at least two polymerizable double bonds in its molecule, such as N,N'-methylenebisacrylamide, (poly)ethylene glycol di(meth)acrylate, (polyoxyethylene)trimethylolpropane tri(meth)acrylate, and poly(meth)acryloxyalkane may be cited. The reactive crosslinking agent may include polyglycidyl ethers such as ethylene glycol diglycidyl ether; covalent cross-linking agents, such as polyhydric alcohols such as propanediol, glycerin, and sorbitol; and cross-linking agents having ion binding property, such as polyvalent metal compounds including aluminum salts can be exemplified. Among these, from the viewpoint of water absorption performance, polymerizable crosslinking agents capable of polymerizing with acrylic acid are preferred, and particularly, acrylate-type, allyl-type, and acrylamide-type polymerizable crosslinking agents are suitably used. These internal crosslinking agents may be used singly, or two or more kinds may be used in combination. The amount of used internal crosslinking agent is preferably 0.001% to 5% by mole, more preferably 0.005% to 2% by mole, still more preferably 0.01% to 1% by mole, and particularly preferably 0.03% to 0.5% by mole, relative to the amount of monomer(s) described above excluding a crosslinking agent in view of the physical properties. Further, the internal crosslinking agent may be added to the aqueous monomer solution before polymerization or may be added to the hydrogel during polymerization or after polymerization, or two of these may be applied in combination. However, it is preferable to add the internal crosslinking agent to the aqueous monomer solution.

(d) Methoxyphenols

In this invention, it is preferable that methoxyphenols be included in the monomer, and it is more preferable that p-methoxyphenol be included, from the viewpoint of polymerization stability. A content of methoxyphenols is preferably 1 ppm to 250 ppm, more preferably 5 ppm to 200 ppm, still more preferably 10 ppm to 160 ppm, and particularly preferably 20 ppm to 100 ppm, relative to the monomer (acrylic acid).

(e) Another Component in Aqueous Monomer Solution

In order to improve various physical properties of the water absorbent resin obtainable by this invention, the following substance (s) can be added as an optional component to the aqueous monomer solution. Specifically, a water-soluble resin or water absorbent resin, such as starch, polyacrylic acid (salt), polyvinyl alcohol, and polyethyleneimine can be added in an amount of, for example, 0% to 50% by weight, preferably 0% to 20% by weight, more preferably 0% to 10% by weight, and still more preferably 0% to 3% by weight, relative to the monomer. The lower limit of the amount of added optional component in the case of adding the optional component is appropriately determined in accordance with the kind, purpose, and effect thereof, and is not particularly limited. The lower limit is preferably about 0.001% by weight relative to the monomer.

Further, an additive such as various foaming agents (carbonates, azo compounds, air bubbles, and the like), surfactants, various chelating agents, hydroxycarboxylic acids, and reducing inorganic salts can be added in an amount of, for example, 0% to 5% by weight, and preferably 0% to 1% by weight, relative to the monomer(s). The lower limit of the amount of added additive in the case of adding the additive is appropriately determined in accordance with the kind, purpose, and effect thereof, and is not particularly limited. The lower limit is preferably about 0.001% by weight relative to the monomer.

Among these, when it is intended to suppress coloration over time of the water absorbent resin (enhancement of color tone stability in long-term storage under high temperature and high humidity) or to enhance urine resistance (prevention of gel deterioration), a chelating agent, a hydroxycarboxylic acid, and a reducing inorganic salt are preferably used, and a chelating agent is particularly preferably used. The used amount is preferably 10 ppm to 5,000 ppm, more preferably 10 ppm to 1,000 ppm, still more preferably 50 ppm to 1,000 ppm, and particularly preferably 100 ppm to 1,000 ppm, relative to the water absorbent resin. In regard to the chelating agents, hydroxycarboxylic acids, and reducing inorganic salts, compounds disclosed in WO 2009/005114 A, EP 2 057 228 B, and EP 1 848 758 B are used.

(f) Polymerization Initiator

The polymerization initiator used in this invention is appropriately selected depending on the polymerization form, and is not particularly limited. Examples include a thermal decomposition-type polymerization initiator, a photodecomposition-type polymerization initiator, and a redox-type polymerization initiator and like. Specific examples of the thermal decomposition-type polymerization initiator include persulfates such as sodium persulfate, potassium persulfate, and ammonium persulfate; peroxides such as hydrogen peroxide, t-butyl peroxide, and methyl ethyl ketone peroxide; and azo compounds such as 2,2'-azobis(2-amidinopropane)dihydrochloride, 2,2'-azobis[2-(2-imidazolin-2-yl)propane]dihydrochloride and like. Examples of the photodecomposition-type polymerization initiator include benzoin derivatives, benzyl derivatives, acetophenone derivatives (for example, 1-hydroxycyclohexyl phenyl ketone), benzophenone derivatives, and azo compounds and like. Examples of the redox-type polymerization initiator include a system which uses a reducing compound such as L-ascorbic acid or sodium hydrogen sulfite in combination with the persulfate salt or peroxide. According to a preferred embodiment, the thermal decomposition-type polymerization initiator and the photodecomposition-type polymerization initiator may be used in combination. The amount of used polymerization initiator is preferably 0.0001% to 1% by mole, and more preferably 0.001% to 0.5% by mole, relative to the monomer. The amount of used polymerization initiator larger than 1% by mole would cause coloration of the water absorbent resin, which is not preferable. The amount of used polymerization initiator less than 0.0001% by mole would increase of residual monomer(s), which is not preferable.

Instead of using the polymerization initiator, polymerization may also be carried out by irradiation with active energy ray such as radiation, electron beam, or ultraviolet radiation. Alternatively, polymerization may also be carried out by using the active energy rays and the polymerization initiator in combination.

(g) Polymerization Method

In this invention, in polymerizing the aqueous monomer solution, aqueous solution polymerization or reverse phase suspension polymerization is usually employed from the viewpoints of water absorption performance of the resultant water absorbent resin or easy polymerization control and like. Preferably, aqueous solution polymerization is used, and more preferably continuous aqueous solution polymerization is employed. Among others, this method is preferably applied to the production in a huge scale with a large production per line of the water absorbent resin. The production is preferably 0.5 [t/hr] or greater, more preferably 1 [t/hr] or greater, still more preferably 5 [t/hr] or greater, and particularly preferably 10 [t/hr] or greater.

Further, preferred embodiments of the aqueous solution polymerization include continuous belt polymerization (for example, U.S. Pat. No. 4,893,999, U.S. Pat. No. 6,241,928 and US Publication No. 2005/215734 or the like), and continuous kneader polymerization (for example, U.S. Pat. No. 6,987,151, U.S. Pat. No. 6,710,141 or the like) and like.

In the continuous aqueous solution polymerization, high temperature initiated polymerization in which the polymerization initiation temperature is set preferably to 30° C. or higher, more preferably 35° C. or higher, still more preferably 40° C. or higher, and particularly preferably 50° C. or higher (the upper limit is a boiling point); or high monomer concentration polymerization in which the monomer concentration is set preferably to 35% by weight or greater, more preferably 40% by weight or greater, and still more preferably 45% by weight or greater (the upper limit is a saturation concentration), may be mentioned as the most preferred examples. The polymerization initiation temperature is defined as a temperature of a solution immediately before the aqueous monomer solution is supplied to a polymerization reactor. The conditions and like disclosed in U.S. Pat. No. 6,906,159, U.S. Pat. No. 7,091,253, and the like can be preferably applied to this invention.

Although the polymerization can be carried out in an air atmosphere, from the viewpoint of preventing coloration, the polymerization is preferably carried out in an inert gas atmosphere such as nitrogen and argon (for example, oxygen concentration: 1% by volume or less). It is preferable to perform polymerization prior to replacement of dissolved oxygen in a monomer or a solution containing a monomer with an inert gas (for example, dissolved oxygen concentration: less than 1 mg/L). The polymerization can be carried out under any pressure, such as under reduced pressure, under normal pressure, or under pressure.

(2-2) Hydrogel Fine Granulation (Crushing) Step

The present step is a step of crushing the hydrogel obtained in the polymerization step, to obtain a hydrogel in a particulate form (hereinafter, referred to as "particulate hydrogel").

The hydrogel obtained in the polymerization step may be directly subjected to drying, but preferably, the hydrogel is subjected to gel crushing as necessary, during polymerization or after polymerization, by using a crusher (a kneader, a meat chopper, a cutter mill, or the like), and is converted to a particulate form. Specifically, a hydrogel fine granulation (hereinafter, also referred to as "gel crushing") step may further be included between the polymerization step by continuous belt polymerization or continuous kneader polymerization and the drying step. In this case, even the case in which the gel is subjected to fine granulation by dispersion in a solvent in the polymerization such as reverse phase suspension polymerization, is also intended to be included in the fine granulation of this invention (fine granulation of the polymerization step), and the gel is suitably crushed by using a crusher. In the fine granulation (crushing) step, incorporation of the additive and the like to the hydrogel, post-neutralization of the acid group in polyacrylic acid (salt), and post-crosslinking of polyacrylic acid (salt) may also be carried out. The final neutralization ratio and the amount of internal crosslinking agent may be in the ranges as described above, and in the post-neutralization after polymerization, sodium hydroxide or (hydrogen) carbonate described in the section "(b) Salt of neutralization", or an aqueous solution or aqueous dispersion thereof may be used. In the post-crosslinking after polymerization, (poly)ethylene glycol diglycidyl ether, or a crosslinking agent capable of reacting with a carboxyl group, such as a water-soluble polyvalent metal salt, which are described in the section (c) "Crosslinking agent (internal crosslinking agent)", can be appropriately used.

In regard to a temperature of the hydrogel in the gel crushing, the hydrogel is kept warm or heated preferably at 40° C. to 95° C., and more preferably 50° C. to 80° C., in view of physical properties. A resin solid content of the particulate hydrogel during gel crushing or after crushing is not particularly limited. In view of physical properties, the resin solid content is 35% to 75% by weight. In the gel crushing step, water, a polyhydric alcohol, a mixed solution of water and a polyhydric alcohol, an aqueous solution of a polyvalent metal, or vapor thereof and like may also be added as necessary, for the purpose of enhancing crushing efficiency. In the case of crushing a hydrogel at a high solid content concentration (for example, 45% to 70% by weight as described below), to which this invention can be preferably applied, air or (好ましくは) dry air can be passed through inside a crushing apparatus.

The weight average particle diameter (D50) of the particulate hydrogel after gel crushing is preferably 0.1 mm to 4 mm, more preferably 0.3 mm to 3 mm, and still more preferably 0.5 mm to 2 mm. The weight average particle diameter (D50) of the particulate hydrogel within the range described above is preferable because drying can be efficiently carried out. A proportion of particulate hydrogel having a particle diameter of 5 mm or larger is preferably 0% to 10% by weight, and more preferably 0% to 5% by weight, relative to the total amount of the particulate hydrogel.

The particle size of the particulate hydrogel can be determined by classifying the particulate hydrogel by using sieves having specific mesh sizes, similarly to the particle size of the water absorbent resin after the pulverization step. The weight average particle diameter (D50) can also be similarly determined. However, in regard to the classification operation of the particulate hydrogel, if measurement is difficult due to aggregation or the like in dry classification method, measurement can be carried out by using a wet classification method described in paragraph of JP 2000-63527 A.

(2-3) Drying Step

This invention has a feature in drying step. Specifically, there is provided a method of drying with a through-circulation dryer a particulate hydrogel polymer having a solid content concentration of 35% to 75% by weight obtainable by polymerizing a partially neutralized salt of acrylic acid with a crosslinking agent in an aqueous solution, wherein drying conditions over a period from a time of introducing the particulate water-containing gel-like crosslinked polymer into a drying zone of the through-circulation dryer to a time of reaching a solid content concentration thereof to 80% by weight, satisfy (1) and (2) as below:

(1) hot air blown to a particulate hydrogel layer has a temperature of 130° C. to 230° C., and a dew point of 50° C. to 80° C.; and (2) difference of temperature (ΔT) between a temperature of hot air blown to a particulate hydrogel layer and a temperature measured after the hot air passes through the particulate hydrogel layer is 20 to 70° C.

The solid content concentration of the particulate hydrogel is usually 35% to 75% by weight, preferably 40% to 70% by weight, and more preferably 45% to 70% by weight. If the solid content concentration is lower than 35% by weight, productivity would be low, as well as the effects characteristic to this invention would appear with difficulties. If the solid content concentration is excessively high, physical properties such as absorption capacity would decrease. The solid content concentration can be determined by a concentration of monomer in the polymerization, evaporation in the polymerization, and by an additive that are added as necessary during polymerization or after polymerization. The solid content concentration may also be controlled by adding a fine powder of a water absorbent resin or a hydrogel thereof as an additive. Hereinafter, the drying step of this invention will be described in detail.

(a) Through-Circulation Type Drying Apparatus

The drying apparatus used in this invention is a through-circulation type drying apparatus, and divided into a batch type and continuous type, which are respectively called as "through-circulation batch type drying apparatuses" and "through-circulation continuous type drying apparatuses". The through-circulation continuous type drying apparatuses may also be referred to as "through-circulation band dryer" or "band type continuous through-circulation dryer" and like. In this invention, among the drying apparatuses described above, a through-circulation continuous type drying apparatus is preferred, and a through-circulation band dryer is more preferred. Hereinafter, a through-circulation band dryer will be described in detail. However, this invention is not intended to be limited to the descriptions given below.

The through-circulation type drying apparatus comprises a wire gauze or a porous plate for loading an object to be dried, and a hot air generating apparatus for blowing hot air in the perpendicular direction (or substantially perpendicular direction) with respect to the object to be dried, the wire gauze or porous plate. A through-circulation continuous type drying apparatus comprises an endless conveyor formed from a wire gauze or a porous plate, and preferably further comprises plural drying chambers that are divided with inner walls which has a structure capable of passing hot air into each of the drying chambers.

In the through-circulation batch type drying apparatus, an object to be dried is taken in and out in a batch mode, while in the through-circulation continuous type drying apparatus, an object to be dried is loaded on an endless belt, subsequently dried in the respective drying chambers, dropped at the turned edge of the belt conveyor, and removed out of the system.

The belt length of the endless conveyor of the through-circulation continuous type drying apparatus is not particularly limited. The belt length is usually in the range of 5 m to 100 m, preferably 10 m to 70 m, and more preferably 20 m to 60 m. The belt width is also not particularly limited. The belt width is usually in the range of 0.5 m to 10 m, and preferably 1 m to 5 m. The ratio of the length direction to the width direction can also be appropriately determined in view of purpose; however, the traveling direction is longer than the width, and the ratio of the length direction to the width direction is appropriately determined usually within 3 to 500 times, and preferably 5 to 100 times.

For the through-circulation belt used in the endless conveyor of the through-circulation continuous drying apparatus, a wire gauze or a punching metal, each having a mesh size of 45 μm to 1,000 μm, may be used. Preferably, a punching metal is used. There are no particular limitations on the shape of the openings of the punching metal, and examples include a circular hole, an elliptical hole, a square hole, a hexagonal hole, an oval hole, a rectangular hole, a rhombic hole, and a cross hole, and combinations of plural shapes of these may also be used. The arrangement of the holes is also not particularly limited, and for example, the holes may be arranged in zigzags or in parallel. The holes may also be sterically formed such as in the form of louver (bay window), but preferably, the holes have a planar structure. Also, there are no particular limitations on the pitch direction of the holes, and for example, the pitch direction may be a longitudinal direction, a transverse direction, or an oblique direction with respect to the traveling direction of the endless conveyor, or combinations thereof may also be used. A wire gauze or a punching metal of the same specifications as the endless belt used in a through-circulation continuous type drying apparatus can also be used in the through-circulation batch type drying apparatus.

A speed of an object to be dried (particulate hydrogel) introduced to move on an endless conveyor of the through-circulation continuous drying apparatus may be appropriately adjusted depending on production, belt length, belt width, and drying time. From the viewpoints of load on a conveyor driving apparatus, durability, and the like, the speed is preferably 0.3 to 5 [m/min], more preferably 0.5 to 2.5 [m/min], still more preferably 0.5 to 2 [m/min], and particularly preferably 0.7 to 1.5 [m/min].

In order to achieve this invention, it is preferable to vary a temperature, a dew point, and an air volume of hot air blown to a particulate hydrogel layer, in multiple stages. Accordingly, it is preferable to use a through-circulation continuous type drying apparatus having multiple chambers. The number of chambers for drying is preferably 5 chambers or more, more preferably 6 chambers or more, and particularly preferably 8 chambers or more. A size of the respective drying chambers (in other words, a length in the travel direction of a belt) may be identical or may be different. The hot air may be blown so as to pass vertically (downward from the above, or upward from the below) through the particulate hydrogel layer obtained in the (2-2) and the like. The upper limit of the number of dry chambers may be appropriately set in accordance with the production or the like, but usually, about 20 chambers are sufficient. A through-circulation band dryer having multiple chambers is illustrated in Patent Literature 2, FIG. 2 of Patent Literature 3, or in FIG. 3.6 of Non-Patent Literature 1. The through-circulation type drying apparatus (through-circulation band dryer) is produced and sold in Japan by Kurimoto, Ltd., Kumeta Seisakusho Co., Ltd., Dalton Co., Ltd., Fuji Paudal Co., Ltd., and Okawara Manufacturing Co., Ltd., for example.

In an industrial-scale experiment using a through-circulation continuous drying apparatus such as a through-circulation band dryer, continuous drying of a large quantity (usually 0.5 [t/hr] or more, further 1 [t/hr] or more, and particularly 5 [t/hr] or more) and production for several hours or several days are generally required. However, since physical properties of the water absorbent resin obtainable in the case of setting drying conditions constant exhibit almost the same behavior in both continuous drying and batch drying, batch type drying can be adopted as a simulation test for continuous drying. Specifically, operating conditions of a through-circulation band dryer can be determined by carrying out a drying experiment in a small scale (several kilograms to several ten kilograms per batch) as a model experiment of continuous drying, and then checking correlation between continuous drying in a large scale and batch drying in a small scale. For example, it is also possible to apply the drying conditions in the through-circulation stationary batch type dryer of Examples 1 and 2 described below, directly to those in drying step in a through-circulation band dryer. By determining drying conditions in a through-circulation band dryer based on drying results in a through-circulation stationary batch type dryer, a scale of drying amount per unit hour can be easily increased by 10 times or more, 100 times or more, or 200 to 10,000 times.

(b) Drying Conditions Up to Solid Content Concentration of 80% by Weight

The present inventors of this invention have found that in the drying step, the drying conditions in 60% or more of a period from a time of introducing the particulate water-containing gel-like crosslinked polymer into a drying zone of the through-circulation dryer to a time of reaching a solid content concentration thereof to 80% by weight are critical to physical properties of the resultant water absorbent resin.

Specifically, it is contemplated that in the drying step of a particulate water-containing gel-like crosslinked polymer according to this invention, not only water contained in the particulate water-containing gel-like crosslinked polymer evaporates, but also, at least one of the chemical reactions listed below occurs simultaneously with the drying of the particulate water-containing gel-like crosslinked polymer.
1. Progress of polymerization
(A) Radical generation due to decomposition of a polymerization initiator
(B) Radical addition polymerization
2. Degradation/deterioration of polymer
(A) Degradation of polymer main chain
(B) Degradation of crosslinked part
(C) Coloration due to oxidation
3. Crosslinking between polymers They have found that these chemical reactions are largely dependent on drying conditions, particularly in the early stage of the drying step, and among others, a period until a solid content concentration of the particulate hydrogel reaches 80% by weight. For the drying conditions after the solid content concentration exceeds 80% by weight, the conditions that are commonly employed by those ordinarily skilled in the art may be appropriately selected.

In the drying method according to this invention, the period until a solid content concentration of the particulate hydrogel reaches 80% by weight (time, or position in a through-circulation band dryer) may be determined from the actual measurement values of the particulate hydrogel, or may be determined with a measuring instrument (moisture meter) installed inside the drying apparatus. Alternatively, a drying time (position) when a solid content concentration of the particulate hydrogel reaches 80% by weight can be determined by measuring a solid content concentration of a particulate hydrogel per unit time, and making a plot of change in solid content concentration over time. The change in solid content concentration of a particulate hydrogel per unit time is illustrated in FIG. 3.7 of Non-Patent Literature 1.

In the drying method of this invention, when air is passed in the perpendicular direction with respect to the particulate hydrogel in a through-circulation band dryer, a solid content concentration (moisture content) may vary along the thickness (for example, 1 cm to 20 cm) direction of a gel layer, even at the same drying time (the same position in a band dryer). In this case, it is desirable to take samples at several different sites in the thickness direction, and to define "80% by weight" in this invention by the average solid content concentration. The solid content concentration of this invention may be measured by other methods, as long as the same solid content concentration as that obtained by a weight loss on drying method described in the Examples (weight loss on drying at 180° C. for 24 hours).

In the drying method according to this invention, as the drying conditions for 60% or more of a period until a solid content concentration of the particulate hydrogel reaches 80% by weight, a temperature of hot air blown to a particulate hydrogel is 130° C. to 230° C., preferably 140° C. to 220° C., more preferably 150° C. to 210° C., and still more preferably 160° C. to 200° C. If the temperature of hot air is below 130° C., a drying rate would be slow, which is economically inefficient. On the other hand, if the temperature of hot air is above 230° C., there would be a risk that physical properties of the water absorbent resin may decrease due to localized overheating.

A dew point of hot air is particularly important for physical properties of the water absorbent resin. In at least a part of the drying time required for the solid content concentration to reach 80% by weight, that is, over 60% or more, 70% or more, 80% or more, and 90% or more of the drying time preferably in this order, and particularly preferably 100% of the drying time, the dew point of hot air used is necessarily 50° C. to 80° C., and preferably 55° C. to 75° C. In the case of changing the temperature or dew point of hot air for every drying part, it may be continuously changed after every lapse of a certain time in a batch type drying system. In a through-circulation continuous drying system composed of multiple chambers, the temperature or dew point may be changed in each of the drying chambers where hydrogel on a belt continuously passes.

For the purpose of increasing a drying speed or the like, a part in which a dew point is below 50° C. may be provided. In this case, the lower limit of the dew point is preferably 10° C. or higher, and more preferably 20° C. or higher, from the viewpoint of reducing residual monomers.

In order to adjust the difference of temperature (ΔT) of hot air, which is essential for this invention, within 20° C. to 70° C., it is preferable to vary a temperature and/or dew point of used hot air in multiple stages. Although the variation thereof is not particularly limited, the temperature and/or dew point is varied at a temperature width or dew point width of preferably 1° C. or greater, more preferably 2° C. or greater, and still more preferably 3° C. or greater, per minute of drying time, or per drying chamber.

If the dew point of hot air does not reach 50° C. over a period from a time of starting to dry to a time of reaching a solid content concentration thereof to 80% by weight (over less than 40%, or less than 30%, of the drying period), the solid content concentration would increase before the temperature of particulate hydrogel rapidly increases, and polymerization in the drying step would not sufficiently proceed, which would induce increase in residual monomers. On the other hand, the dew point of the hot air higher than 80° C. would induce deterioration of color of the resultant water absorbent resin, as well as cause decrease in water absorption. It is preferable to control a speed of hot air to 3.0 [m/sec] or less, and more preferably to 0.5 to 2.0 [m/sec]. A direction of hot air may be upward or downward relative to the particulate hydrogel. Although there are no particular limitations, in the case of using a through-circulation band dryer, it is preferable to use an upward flow and a downward flow in combination, and it is particularly preferable to use an upward flow (up-flow) for former half part of the dryer and a downward flow (down-flow) for latter half part of the dryer. By performing drying under such conditions, more uniform drying can be achieved.

In the drying method according to this invention, it is necessary to set a difference of temperature (ΔT) between a temperature of hot air blown to a particulate hydrogel layer and a temperature measured after the hot air passes through the particulate hydrogel layer to 20° C. to 70° C., and preferably 30° C. to 60° C., over a period until a solid content concentration of a particulate hydrogel reaches 80% by weight (essentially 60% or more, preferably 70% or more, more preferably 80% or more, and still more preferably 90% or more, of the drying period, and particularly preferably, substantially the whole period). If the temperature difference over a period until a solid content concentration of a particulate hydrogel reaches 80% by weight (less than 40%, preferably less than 30%, more preferably less than 20%, and still more preferably less than 10%, of the drying period) is less than 20° C., productivity would not improve. Also, if the temperature difference over a period until a solid content concentration of a particulate hydrogel reaches 80% by weight (less than 40%, preferably less than 30%, more preferably less than 20%, and still more preferably less than 10%, of the drying period) is greater than 70° C., it is speculated that heat transfer from hot air to a particulate hydrogel would be rapid, which would induce non-uniform heating or partial overheating between the dried sites. Thus, in such case, a proportion of non-uniform drying would be increased, and it would be difficult to obtain a water absorbent resin having desired physical properties, which is not preferable.

The temperature of hot air blown to a particulate hydrogel layer is usually measured at a site immediately before a hot air inlet port of a dryer (for example, within 1 m from the inlet port, and still more preferably, at a pipe within 0.2 m). A temperature measured after the hot air as defined in the present application passes through the particulate hydrogel layer is usually measured at a thermometer provided immediately above a particulate hydrogel layer, or at a site immediately before a discharge port of hot air (for example, within 1 m from the discharge port, and still more preferably, at a pipe within 0.2 m). The measurement of a dew point may be carried out at the same site as the temperature measurement. In this invention, as illustrated in FIG. 1, a temperature of hot air blown to a particulate hydrogel layer is a temperature measured at point A, which is 0.1 m away from a hot air inlet port of a dryer (a hot air inlet port 9 of a through-circulation dryer 8 in FIG. 1). Also, as illustrated in FIG. 1, a temperature measured after hot air passes through a particulate hydrogel layer is a temperature measured at point B, which is 0.1 m away from a hot air discharge port of a dryer (a hot air discharge port 10 of a through-circulation dryer 8 in FIG. 1).

In a through-circulation batch type drying apparatus, a temperature and a dew point of hot air may be measured against a drying time. Also, in a through-circulation continuous type drying apparatus, a temperature and a dew point of hot air may be measured at a predetermined position on a through-circulation belt (as defined in the drying time). Furthermore, in the through-circulation band dryer having multiple chambers, a temperature and a dew point can be measured at each drying chamber having a hydrogel pass on a belt continuously.

In regard to a method of controlling the temperature difference of hot air as defined in the present application to 20° C. to 70° C., the temperature difference may be adjusted to 20° C. to 70° C. according to any arbitrary method, and there are no particular limitations. It is preferable to appropriately select one or two or more of (1) to (7) listed below, and among them, it is more preferable to control a thickness of a gel layer as in (1).

(1) Thickness of Particulate Hydrogel Layer Deposited on Belt

For example, according to this invention, a thickness of a particulate hydrogel layer deposited on a belt is preferably about 10 mm to about 90 mm, and more preferably about 20 mm to about 60 mm. When the thickness is in such a range, a temperature difference of hot air can be easily controlled within the range described above, drying efficiency or various physical properties of a water absorbent resin can be improved, particularly, a bulk specific gravity of a water absorbent resin can be controlled to a high level.

(2) Temperature of Particulate Hydrogel Layer Deposited on Belt

For example, according to this invention, a temperature of a particulate hydrogel immediately before being introduced into a drying zone (immediately before drying) is not particularly limited. It is preferably 40° C. to 70° C., and still more preferably 45° C. to 60° C. When the temperature is in such a range, a temperature difference of hot air is small, unevenness does not easily occur in physical properties of a dried product, and color tone deterioration or decrease in absorption capacity of a water absorbent resin can be suppressed.

(3) Bulk Specific Gravity (Degree of Compression) of Particulate Hydrogel Layer Deposited on Belt For example, according to this invention, a bulk specific gravity (degree of compression) of a particulate hydrogel layer deposited on a belt is not particularly limited as long as a degree of compression that would give the thickness of a particulate hydrogel layer deposited on a belt as defined in (1) can be attained. The bulk specific gravity can be appropriately selected in accordance with permeability of hot air or ease of scattering of a particulate hydrogel. If the bulk specific gravity is too high, permeability of hot air would be deteriorated, which would cause drying unevenness. On the contrary, if the bulk specific gravity is too small, a particulate hydrogel would be easily scattered by hot air.

(4) Particle Size Distribution of Particulate Hydrogel Polymer

For example, according to this invention, a particle size distribution of a particulate hydrogel polymer is not particularly limited as long as a particle size distribution capable of obtaining a weight average particle diameter (D50) of a base polymer described in the following (2-4) can be attained. Specifically, the weight average particle diameter (D50) of a particulate hydrogel polymer is preferably 0.1 mm to 4 mm, more preferably 0.3 mm to 3 mm, and still more preferably 0.5 mm to 2 mm. When the weight average particle diameter is in such a range, a temperature difference of hot air is small, unevenness does not easily occur in physical properties of a dried product, and color tone deterioration or decrease in absorption capacity of a water absorbent resin can be suppressed.

(5) Moisture Content of Particulate Hydrogel Polymer

For example, according to this invention, a moisture content of a particulate hydrogel polymer is defined by a solid content concentration of the particulate hydrogel, and is usually 25% to 65% by weight, preferably 30% to 60% by weight, and more preferably 30% to 55% by weight.

(6) Linear Velocity of Hot Air

For example, according to this invention, a linear velocity of hot air is not particularly limited as long as a moisture content percentage defined in (5) can be achieved. The linear velocity is preferably 3.0 m/sec or less, and more preferably 0.5 m/sec to 2.0 m/sec. When the linear velocity is in such a range, a temperature difference of hot air is small, unevenness does not easily occur in physical properties of a dried product, while the moisture content of the particulate hydrogel polymer may be adjusted within an appropriate range. Also, color tone deterioration or decrease in absorption capacity of a water absorbent resin can be suppressed.

(7) Area Ratio Occupied by Particulate Hydrogel Polymer on Belt

For example, according to this invention, an area ratio occupied by a particulate hydrogel polymer on a belt is not particularly limited, but the particulate hydrogel polymer is preferably deposited in an area of about 0.85 m$^2$ to 1 m$^2$, and more preferably laminated in an area of about 0.90 m$^2$ to 0.98 m$^2$, relative to 1 m$^2$ of a surface area of belt. When the area ratio is in such a range, hot air can be uniformly and efficiently blown to a particulate hydrogel polymer, a temperature difference of hot air is small, unevenness does not easily occur in physical properties of a dried product, and color tone deterioration or decrease in absorption capacity of a water absorbent resin can be suppressed.

(c) Material of Through-Circulation Belt or the Like

A through-circulation belt may be formed as a single belt, plural belts, or a multiple-step or multiple-step apparatus. According to this invention, operation of a belt dryer having at least one belt is advantageously used. A single belt dryer is particularly advantageously used. A specific surface treatment such as electropolishing or a Teflon (registered trademark) treatment can also be carried out. Among others, a material of a punching metal is preferably stainless steel. A thickness of a belt is appropriately determined usually within 0.3 mm to 10 mm, and preferably 1 mm to 5 mm.

A surface roughness of a belt surface is controlled so as to give a surface roughness (Rz) defined by JIS B 0601-2001 of 800 nm or less. A surface of a belt is preferably smoothened so as to give a surface roughness (Rz) of preferably 500 nm or less, more preferably 300 nm or less, still more preferably 200 nm or less, particularly preferably 185 nm or less, and most preferably 170 nm or less. As used herein, the surface roughness (Rz) means a maximum of maximum height (μm) of surface irregularities. A lower limit of the surface roughness (Rz) is 0 nm, but there is no large difference even at a surface roughness of about 10 nm, and a surface roughness of about 10 nm or 20 nm is also sufficient. Another surface roughness (Ra) is also defined by JIS B 0601-2001, and the preferred value thereof is considered to be the same as Rz. More preferably, Ra is 250 nm or less, and particularly preferably 200 nm or less. The lower limit of the surface roughness (Ra) is 0 nm, but there is no large difference even at a surface roughness of about 10 nm.

Such surface roughness can be measured according to JIS B 0651-2001 by using a probe type surface roughness measuring instrument.

(d) Additives for Drying Step

In the drying step of this invention, the additives and the like listed as examples in (2-1) (e) may be added in accordance with the purpose. A fine powder (particularly, a fine powder containing 70% by weight or more of a powder having a particle size of 150 μm or less) obtainable by a fine powder recycling step described in the following (2-6) may also be added to a particulate hydrogel before drying in an amount of 1% to 40% by weight, further 10% to 30% by weight (relative to solids content).

(2-4) Pulverization Step and Classification Step (Particle Size after Drying and Adjustment)

The present step is a step for pulverizing and classifying the dried product obtained in the drying step described above, to obtain a base polymer.

In the present step, the dried product obtained in the drying step can be directly used as a dry powder, but it is preferable to control the dried product to have a particular particle size in order to enhance physical properties in a surface crosslinking step that will be described below. The control of particle size is not limited to this pulverization step and classification step, and can be appropriately carried out in the polymerization step (particularly, reverse phase suspension polymerization), a fine powder collection step, a granulation step, and the like. Hereinafter, the particle size is defined by standard sieves (JIS Z8801-1 (2000)).

A pulverizer that can be used in the present pulverization step is not particularly limited, and those conventionally known as a pulverizer can be used. Specific examples include a roll mill, a hammer mill, a roll granulator, a jaw crusher, a gyratory crusher, a cone crusher, a roll crusher, and a cutter mill and the like. Among these, from the viewpoint of particle size control, it is preferable to use a multistage roll mill or a roll granulator.

For a classification step, various classifiers such as sieve classification and air stream classification can be used.

From the viewpoint of enhancing physical properties of a water absorbent resin obtainable by the present step, it is preferable to control the water absorbent resin to have the following particle size. Specifically, a weight average particle diameter (D50) of a base polymer is preferably 200 μm to 600 μm, more preferably 200 μm to 550 μm, still more preferably 250 μm to 500 μm, and particularly preferably 350 μm to 450 μm. A proportion of fine particles (having a particle size of less than 150 μm) that pass through a sieve having a mesh size of 150 μm (JIS standard sieve) is preferably 0% to 5% by weight, more preferably 0% to 3% by weight, and still more preferably 0% to 1% by weight, relative to the total amount of base polymer. A proportion of large particles (having a particle size of greater than 850 μm) that do not pass a sieve having a mesh size of 850 μm (JIS standard sieve) is preferably 0% to 5% by weight, more preferably 0% to 3% by weight, and still more preferably 0% to 1% by weight, relative to the total amount of base polymer. A logarithmic standard deviation (σζ) of particle size distribution of base polymer is preferably 0.20 to 0.40, more preferably 0.25 to 0.37, and still more preferably 0.27 to 0.35. These particle sizes can be measured by a method disclosed in WO 2004/69915 A and EDANA-ERT420.2.-02 (Particle Size Distribution).

(2-5) Surface Crosslinking Step

A crosslinked polymer (base polymer) obtained by the drying step may be subjected to surface crosslinking. Specifically, this invention includes a method for producing a water absorbent resin, which further comprises surface crosslinking after the drying according to this invention.

The present step is a step of crosslinking a vicinity of surface of base polymer obtained in the pulverization step and classification step by using a surface crosslinking agent (surface crosslinking reaction) as necessary for enhancement of water absorption, and through the surface crosslinking, the effects by this invention can be more conspicuously exhibited. Meanwhile, Patent Literature 1 is an invention of a method for reducing residual monomers, and Patent Literatures 3 and 4 are technologies related to a band drying method leaving no undried substances. However, Patent Literatures 1, 3, and 4 do not provide any disclosure on surface crosslinking, absorbency against pressure, or liquid permeability. Specifically, a water absorbent resin having a high degree of whiteness with less coloration, which is not specified in Patent Literatures 1 to 4, may be obtained by the specific drying of the present application and this surface cross linking treatment, and the steps are preferably applied to a water absorbent resin at high temperature surface crosslinking. When the water absorbent resin obtainable by this invention is used as a raw material of a sanitary product (paper diapers in particular), it is desirable to decrease absorption capacity without load (CRC) (preferably with a decrease by 1 to 10 [g/g]) and to increase AAP (absorbency against pressure) preferably by 20 [g/g] or more, by the present surface crosslinking treatment.

There are no particular limitations on a surface crosslinking agent that can be used in this invention, but various organic or inorganic crosslinking agents may be used. Among them, organic surface crosslinking agents are preferred, and it is more preferable to use an organic surface crosslinking agent and an ionic crosslinking agent in combination. Specific examples include polyhydric alcohol compounds, epoxy compounds, polyvalent amine compounds or condensates thereof with haloepoxy compounds, oxazoline compounds, (mono-, di-, or poly-)oxazolidinone compounds, and alkylene carbonate compounds. Particularly, dehydrated ester-reactive crosslinking agents containing polyhydric alcohol compounds, alkylene carbonate compounds, and oxazolidinone compounds, which need reaction at a high temperature, can be used. More specifically, the compounds listed as examples in U.S. Pat. No. 6,228,930, U.S. Pat. No. 6,071,976, U.S. Pat. No. 6,254,990, and the like can be used. Examples include polyhydric alcohol compounds such as mono-, di-, tri- tetra-, or propylene glycol, 1,2-propanediol, 1,3-propanediol, glycerin, 1,4-butanediol, 1,3-butanediol, 1,5-pentanediol, 1,6-hexanediol, and sorbitol; epoxy compounds such as ethylene glycol diglycidyl ether and glycidol; alkylene carbonate compounds such as ethylene carbonate; oxetane compounds; and cyclic urea compounds such as 2-imidazolidinone and the like. An amount of used surface crosslinking agent is appropriately determined in the range of preferably 0.001 to 10 parts by weight, and more preferably 0.01 to 5 parts by weight, relative to 100 parts by weight of a base polymer.

It is preferable to use water as a solvent in mixing a water absorbent resin with a surface crosslinking agent. An amount of used water is appropriately determined in the range of preferably 0.5 to 20 parts by weight, and more preferably 0.5 to 10 parts by weight, relative to 100 parts by weight of a base polymer. Also, a hydrophilic organic solvent may be used in combination as necessary, in addition to water. An amount thereof is appropriately determined in the range of preferably 0 to 10 parts by weight, and more preferably 0 to 5 parts by weight, relative to 100 parts by weight of a base polymer.

In mixing of a surface crosslinking agent solution, a water-insoluble fine particle powder or a surfactant may be incorporated to an extent that effects by this invention are not impaired. In regard to a kind or amount of the fine particle powder or surfactant and the like, examples are given in U.S. Pat. No. 7,473,739 and the like. The amount is appropriately determined in the range of preferably 0 to 10 parts by weight, more preferably 0 to 5 parts by weight, and still more preferably 0 to 1 part by weight, relative to 100 parts by weight of a base polymer.

In the present step, after a base polymer and a surface crosslinking agent are mixed, the mixture is preferably subjected to heat treatment, and subsequently to cool treatment as necessary. A heating temperature in the heat treatment is preferably 70° C. to 300° C., more preferably 120° C. to 250° C., and still more preferably 150° C. to 250° C. The treatment temperature of lower than 70° C. would induce increase in heat treatment time and decrease in productivity, and also prevent a uniform surface crosslinked layer from being formed, which is not preferable. If the treatment temperature is higher than 300° C., a base polymer would be deteriorated, and it is not preferable. A heating time in the heat treatment is preferably in the range of 1 minute to 2 hours. The heat treatment can be carried out in a conventional dryer or a conventional heating furnace.

The surface crosslinking method disclosed in EP 0 349 240 B, EP 0 605 150 B, EP 0 450 923 B, EP 0 812 873 B, EP 0 450 924 B, EP 0 668 080 B, JP 7-242709 A, JP 7-224304 A, U.S. Pat. No. 5,409,771, U.S. Pat. No. 5,597,873, U.S. Pat. No. 5,385,983, U.S. Pat. No. 5,610,220, U.S. Pat. No. 5,633,316, U.S. Pat. No. 5,674,633, U.S. Pat. No. 5,462,972, WO 99/42494 A, WO 99/43720 A, WO 99/42496 A, and the like can be preferably applied to this invention.

(2-6) Another Steps

In addition to the steps described above, a surface treatment step with a polyvalent metal, a recycling step of evaporated monomers, a granulation step, a fine powder removal step, a fine powder recycling step, and the like may be optionally provided. Further, for the purpose of a stability effect of color tone over time or prevention of gel deterioration and the like, an additive described above may be used in a monomer or polymerization product thereof in any one or all of the various steps described above.

The surface treatment step with a polyvalent metal salt can be applied when high liquid permeability under pressure (SFC or GBP) is demanded. For example, production methods described in U.S. Pat. No. 6,605,673 and U.S. Pat. No. 6,620,899 can be applied as necessary.

The production method of this invention may preferably include a fine powder recycling step. The fine powder recycling step is referred to as a step of separating a fine powder (particularly, a fine powder containing 70% by weight or more of a powder having a particle size of 150 μm or less) that is generated in a drying step and if necessary, a pulverization step and a classification step, and then recycling the fine powder to a polymerization step or a drying step directly or after hydration. The methods described in US 2006/247,351 A and U.S. Pat. No. 6,228,930 can be applied. When the fine powder is recycled, a particle size of base polymer can be controlled, and at the same time, a high solid content concentration can be easily achieved by addition of the fine powder. Further, a dried product can be easily detached from a through-circulation belt of a dryer, which is preferable.

In the conventional drying methods, in regard to a water absorbent resin obtained by the production method which includes a fine powder recycling step, it has been difficult to obtain a water absorbent resin having superior physical properties because of non-uniform drying associated with added fine powder, increase in residual monomers, decrease in water absorption, and the like. In the drying method of this invention, particularly in the case of including a fine powder recycling step in the step for producing a water absorbent resin, effect of suppressing decrease in water absorption physical properties or preventing coloration can be excellently manifested.

[3] Physical Properties of Water Absorbent Resin

The water absorbent resin of this invention comprises a polyacrylic acid (salt)-type water absorbent resin as a main component, and is obtained by the polymerization or surface crosslinking and the like described above in the case where the water absorbent resin is to be used in a sanitary product, particularly paper diapers. For the water absorbent resin to be obtained, it is preferable to control at least one or more physical properties among the various physical properties described in the following (3-1) to (3-5), and it is preferable to control two or more, particularly three or more, physical properties including AAP. If the water absorbent resin does not satisfy property (physical properties) described below, it would not exhibit sufficient performance in diapers containing the water absorbent resin at a high concentration as of 40% by weight or more.

(3-1) CRC (Absorption Capacity without Load)

CRC (absorption capacity without load) of the water absorbent resin obtainable by this invention is preferably 10 [g/g] or greater, more preferably 20 [g/g] or greater, still more preferably 25 [g/g] or greater, and particularly preferably 30 [g/g] or greater. The upper limit of CRC is not particularly limited, but is preferably 50 [g/g] or less, more preferably 45 [g/g] or less, and still more preferably 40 [g/g] or less. If the CRC is less than 10 [g/g], absorption capacity of the water absorbent resin would be low, and the water absorbent resin would not be suitable for the use for an absorbent material in a sanitary product such as paper diapers. If the CRC exceeds 50 [g/g], when such a water absorbent resin is used in an absorbent material, there is a risk that sanitary products having an excellent rate of liquid uptake would not be obtained, which is not preferable. Meanwhile, CRC can be appropriately controlled by using an internal crosslinking agent or a surface crosslinking agent and the like described above.

(3-2) AAP (Absorbency Against Pressure)

Regarding AAP (absorbency against pressure) of the water absorbent resin obtainable by this invention, in order to prevent leakage into paper diapers, AAP against pressure of 4.83 kPa (0.7 psi) is preferably 20 [g/g] or greater, more preferably 22 [g/g] or greater, and still more preferably 24 [g/g] or greater, by applying the drying described above as a means for achieving the prevention. The upper limit of AAP is not particularly limited, but in view of balance with other physical properties, AAP is preferably 40 [g/g] or less. When the AAP is less than 20 [g/g], in using such a water absorbent resin in an absorbent material, a sanitary product exhibiting less return of liquid (usually, also referred to as "re-wet") under pressure applied to the absorbent material, would not be obtained, which is not preferable. Meanwhile, AAP can be appropriately controlled by using a surface crosslinking agent or a particle size and the like described above.

(3-3) SFC (Saline Flow Conductivity)

Regarding SFC (saline flow conductivity) of the water absorbent resin obtainable by this invention, in order to prevent leakage into paper diapers, SFC, liquid permeability under pressure, is preferably 20 $[\times 10^{-7}\ cm^3 \cdot s \cdot g^{-1}]$ or greater, more preferably 30 $[\times 10^{-7}\ cm^3 \cdot s \cdot g^{-1}]$ or greater, still more preferably 35 $[\times 10^{-7}\ cm^3 \cdot s \cdot g^{-1}]$ or greater, and particularly preferably 50 $[\times 10^{-7}\ cm^3 \cdot s \cdot g^{-1}]$ or greater, by applying the drying described above as a means for achieving the prevention. The upper limit of SFC is not particularly limited, but in view of balance with other physical properties, SFC is preferably 3,000 $[\times 10^{-7}\ cm^3 \cdot s \cdot g^{-1}]$ or less, and more preferably 2,000 $[\times 10^{-7}\ cm^3 \cdot s \cdot g^{-1}]$ or less. If SFC exceeds 3,000 $[\times 10^{-7}\ cm^3 \cdot s \cdot g^{-1}]$, an absorbent material using such a water absorbent resin would induce liquid leakage therein, which is not preferable. Meanwhile, SFC can be appropriately controlled by the drying method described above or the like.

(3-4) Ext (Extractables)

Ext (extractables) of the water absorbent resin obtainable by this invention is preferably 35% by weight or less, more preferably 25% by weight or less, still more preferably 15% by weight or less, and particularly preferably 10% by weight or less. If Ext is greater than 35% by weight, the water absorbent resin would have weak gel strength and low liquid permeability. Further, in using such a water absorbent resin in an absorbent material, a sanitary product exhibiting less return of liquid (re-wet) under pressure applied to the absorbent material would not be obtained, which is not preferable. Meanwhile, Ext can be appropriately controlled by using an internal crosslinking agent described above or the like.

(3-5) Residual Monomers

Residual monomers of the water absorbent resin obtainable by this invention is controlled, from the viewpoint of safety, preferably to 0 ppm to 400 ppm, more preferably 0 ppm to 350 ppm, still more preferably 0 ppm to 300 ppm, and particularly preferably 0 ppm to 200 ppm. Meanwhile, residual monomers can be appropriately controlled by the polymerization method described above or the like.

[4] Use of Water Absorbent Resin

Use of the water absorbent resin obtainable by the production method according to this invention is not particularly limited, and the water absorbent resin can be used in sanitary products such as paper diapers, sanitary napkins, and incontinence pads; and water absorbent articles such as agricultural and horticultural water retention agents, waste water solidifying agents, and industrial water stopping materials.

The water absorbent resin obtainable by this invention can exhibit especially excellent performance in a water absorbent article using a water absorbent resin at a high concentration. Specifically, a content (core concentration) of a water absorbent resin in an absorbent material in a water absorbent article is preferably 30% to 100% by weight, more preferably 40% to 100% by weight, still more preferably 50% to 100% by weight, further still more preferably 60% to 100% by weight, particularly preferably 70% to 100% by weight, and most preferably 75% to 95% by weight. When the core concentration is set within the range described above, the effects by this invention can be exhibited more effectively, which is preferable. Particularly, when the water absorbent resin obtainable by this invention is used in an upper layer of a water absorbent material in the core concentration range described above, absorbed liquid such as urine can be excellently diffused in therein because of its high liquid permeability (liquid permeability under pressure), and absorption capacity by the water absorbent article as a whole, such as a paper diaper, can be enhanced by efficient liquid distribution, which is preferable. Further, it is also preferable because a water absorbent article having whiteness with a sense of hygiene kept can be provided.

The water absorbent may be preferably compression molded so as to give a density of 0.06 to 0.50 [g/cm$^3$] and a basis weight of 0.01 to 0.20 [g/cm$^2$]. A thickness of the water absorbent is preferably 30 mm or less, more preferably 20 mm or less, and still more preferably 10 mm or less, with which a water absorbent article suitable for thin paper diapers can be provided.

EXAMPLES

Examples

Hereinafter, this invention will be described by reference to Examples, but this invention is not construed to be limited to these Examples. For convenience, "liter" may be indicated as "L", and "% by weight" as "wt %". Unless particularly stated otherwise, various physical properties described in the claims and Examples of a water absorbent resin obtainable by this invention were determined according to the Measurement Examples described below, under conditions of room temperature (20° C. to 25° C.) and humidity of 50 RH %.

1. Resin Solid Content (Solids Content)

In an aluminum cup having a bottom of a diameter of about 50 mm, 1.00 g of a water absorbent resin was weighed, and a total weight W1 [g] of the sample (water absorbent resin and aluminum cup) was accurately weighed.

Subsequently, the sample was placed in an oven at an atmospheric temperature of 180° C., to dry the water absorbent resin. After 3 hours, the sample was removed from the oven and cooled to room temperature in a desiccator. Thereafter, the total weight W2 [g] of the dried sample (water absorbent resin and aluminum cup) was weighed. A solid content concentration (unit: [wt %]) was calculated according to the following formula.

$$\text{Solids Content [wt\%]} = 100 - \frac{(W1 - W2)}{\text{Weight of water absorbent resin [g]}} \times 100 \quad \text{[Mathematical Formula 1]}$$

In the measurement of a resin solid content of a particulate water-containing gel-like crosslinked polymer, the measurement was carried out by the same operation as described above, except that the amount of the hydrogel was set to about 2 to 4 g, and the drying time was changed to 24 hours.

2. SFC (Saline Flow Conductivity)

SFC (saline flow conductivity) of a the water absorbent resin obtainable by this invention was measured according to U.S. Pat. No. 5,669,894.

3. Other Physical Properties

Physical properties such as the CRC (absorption capacity without load), particle size distribution (see "PSD" above: method described in ERT420.2-02), pH extractables (see "Ext": method described in ERT470.2-02), and amount of residual acrylic acid (see "Residual monomers": method described in ERT410.2-02) of a water absorbent resin were measured according to ERT of EDANA, or according to US 2006/204,755 A as mentioned above.

Example 1

An aqueous monomer solution containing acrylic acid, sodium hydroxide, polyethylene glycol diacrylate (average molecular weight: 487), 1-hydroxycyclohexyl phenyl ketone, and water as raw materials was prepared. The contents of acrylic acid, sodium hydroxide, and water were adjusted so as to give a monomer concentration of 45% by weight and a neutralization ratio of acrylic acid of 70% by mole. Polyethylene glycol diacrylate was added to the aqueous monomer solution in an amount of 0.07% by mole relative to acrylic acid, and 1-hydroxycyclohexyl phenyl ketone was added thereto in an amount of 0.01% by weight relative to acrylic acid. After the preparation, a temperature of the aqueous monomer solution was controlled to 95±1° C.

Thereafter, an aqueous solution of sodium persulfate was mixed into the aqueous monomer solution to give an amount of added sodium persulfate of 0.12 g/mol relative to acrylic acid, to yield a monomer mixture solution.

The monomer mixture solution was continuously supplied to a belt polymerization apparatus, to carry out polymerization, to obtain a band-shaped water-containing gel-like crosslinked polymer (hydrogel). The belt polymerization apparatus used in the present Example is a polymerization apparatus which has an endless belt coated with a fluororesin on its surface, and is provided with a UV lamp and a suction pipe for collecting evaporated water.

Then, the band-shaped hydrogel obtained with the polymerization apparatus was continuously crushed with a meat chopper, to yield a crushed particulate hydrogel 1. The solid content concentration of the particulate hydrogel 1 was 56% by weight.

Subsequently, the particulate hydrogel 1 was spread in a hot air dryer (manufactured by Okawara Manufacturing Co., Ltd.; through-circulation dryer, see FIG. 1) 8 to a thickness of 50 mm. The temperature (temperature immediately before drying) of the particulate hydrogel thus spread was 60° C. Then, gases were introduced into a heat exchanger 6 through a fresh air inlet tube 2 and a water vapor inlet tube 3, and the gases were heated by a heat transfer medium introduced through a heat medium inlet tube 7, or alternatively, a portion of the gases were discharged through a discharge tube 4 and then were circulated to the heat exchanger 6 by means of a blower 5, to blow hot air having its temperature and dew point adjusted to the particulate hydrogel at an air speed of 1.6 [m/sec], to dry the particulate hydrogel and to obtain a dry gel.

In drying, using nozzles disposed at positions A and B in FIG. 1, temperature and dew point was measured by using a handy type multifunctional thermohygrometer (rotoronic HYDROPALM2, RotronicAG, Swiss) and HygroClipHK40 as a sensor. In FIG. 1, the position A is located 0.1 m away from the hot air inlet port 9 of the through-circulation dryer 8, and the position B is located 0.1 m away from the hot air discharge port 10 of the through-circulation dryer 8.

A solid content concentration of the particulate hydrogel was measured by repeating the same drying experiment several times, taking out a material when a predetermined drying time had elapsed, to use a sample for the measurement of solid content concentration.

The data thus obtained are shown in Table 1. In Table 1, ΔT represents "(temperature of hot air blown to particulate hydrogel layer)−(temperature of hot air after passing through particulate hydrogel layer and through-circulation belt)". As indicated in Table 1, it was found that substantially throughout the entire drying period until the solid content concentration reached 80% by weight, ΔT was in the range of 20° C. to 70° C. (about 54° C. to 31° C.)

TABLE 1

| Drying time [min] | Temperature[1] of hot air [° C.] | dew point[1] of hot air [° C.] | Discharge temperature[2] [° C.] | ΔT[3] [° C.] | Solid content concentration [wt %] |
|---|---|---|---|---|---|
| 0 | | | | | 56 |
| 2 | 156 | 69 | 102 | 54 | 58 |
| 4 | 168 | 72 | 110 | 58 | 66 |
| 6 | 156 | 58 | 117 | 39 | 73 |
| 8 | 179 | 67 | 148 | 31 | 82 |
| 10 | 187 | 77 | 158 | 29 | 90 |
| 20 | 190 | 40 | 190 | 0 | 96 |
| 40 | 190 | 19 | 190 | 0 | 96 |

[1]Temperature and dew point of hot air blown to particulate hydrogel layer
[2]Temperature of hot air after passing particulate hydrogel layer and through-circulation belt
[3](Temperature of hot air blown to particulate hydrogel layer) − (temperature of hot air after passing particulate hydrogel layer and through-circulation belt)

The dried product obtained by the drying operation described above was pulverized, and then was classified by using JIS standard sieves having a mesh size of 850 μm and 150 μm, obtain a dried product having a particles size of 850 μm to 150 μm as base polymer 1.

The resultant base polymer 1 was mixed with a surface crosslinking agent solution containing 0.48 part by weight of 1,4-butanediol, 0.75 part by weight of 1,2-propanediol, and 4.0 parts by weight of water, relative to 100 parts by weight of the base polymer 1, to obtain a wet product. The wet product was subjected to surface crosslinking by heat treatment at 180° C. for 45 minutes. After the heat treatment, the resultant water absorbent resin particles were pulverized until the particles passed through a JIS standard sieve having a mesh size of 850 μm, to obtain a surface crosslinked water absorbent resin 1. Physical properties of the water absorbent resin 1 thus obtained are shown in Table 4.

Example 2

In a kneader equipped with two Sigma type blades, an aqueous monomer solution containing sodium acrylate, acrylic acid, and water and having a monomer concentration of 38% by weight and a neutralization ratio of 70 mol % was prepared, and polyethylene glycol diacrylate (average number of ethylene glycol units: 9) as an internal crosslinking agent was dissolved therein at a concentration of 0.06 mol % (relative to the monomer).

Next, nitrogen gas was blown into the aqueous monomer solution, and the entire reactor was nitrogen purged, while simultaneously reducing dissolved oxygen in the aqueous monomer solution. Subsequently, while the two Sigma type blades were rotated, 0.12 [g/mol] (relative to the monomer) of sodium persulfate and 0.005 [g/mol] (relative to the monomer) of L-ascorbic acid were added thereto as polymerization initiators, and polymerization was carried out under stirring in the kneader. After about 40 minutes, a crushed particulate water-containing gel-like crosslinked polymer 2 having an average particle size of about 2 mm was obtained. A solid content concentration of the particulate hydrogel 2 was 40% by weight.

Then, the resultant particulate hydrogel 2 was dried by using the same drying apparatus as that used in Example 1. The particulate hydrogel 2 was spread into a gel layer of height of 30 mm. At this time, the temperature (temperature immediately before drying) of the spread particulate hydrogel 2 was 53° C. The particulate hydrogel 2 was dried while temperature and dew point of hot air were adjusted. The data thus obtained are shown in Table 2. As indicated in Table 2, it is noted that substantially throughout the entire drying period until the solid content concentration reached 80% by weight, ΔT was in the range of 20° C. to 70° C. (about 58° C. to 55° C.)

TABLE 2

| Drying time [min] | Temperature[1] of hot air [° C.] | dew point[1] of hot air [° C.] | Discharge temperature[2] [° C.] | ΔT[3] [° C.] | Solid content concentration [wt %] |
|---|---|---|---|---|---|
| 0 | | | | | 40 |
| 3 | 130 | 67 | 72 | 58 | 63 |
| 6 | 130 | 73 | 75 | 55 | 80 |
| 9 | 142 | 68 | 90 | 52 | 90 |
| 15 | 170 | 50 | 150 | 20 | 93 |
| 40 | 170 | 21 | 170 | 0 | 95 |

[1]Temperature and dew point of hot air blown to particulate hydrogel layer
[2]Temperature of hot air after passing particulate hydrogel layer and through-circulation belt
[3](Temperature of hot air blown to particulate hydrogel layer) − (temperature of hot air after passing particulate hydrogel layer and through-circulation belt)

Further, classification, surface crosslinking, and particle size regulation were carried out in the same manner as in Example 1, to obtain a water absorbent resin 2. Physical properties of the water absorbent resin 2 thus obtained are shown in Table 4. However, surface crosslinking was carried out until the same absorption capacity as that obtained in Example 1 (CRC=30 [g/g]) was attained, by regulating a heat treatment time (also called: reaction time) in Example 1.

Comparative Example 1

The particulate hydrogel 1 obtained in Example 1 was dried by using the same drying apparatus as that used in Example 1. The particulate hydrogel 1 was spread into a gel layer of height of 100 mm. At this time, the temperature of the spread particulate hydrogel 1 was 36° C. The particulate hydrogel 1 was dried while temperature and dew point of hot air were adjusted. The data thus obtained are shown in Table 3. However, surface crosslinking was carried out until the same absorption capacity as that obtained in Example 1

(CRC=30 [g/g]) was attained, by regulating a heat treatment time (also called: reaction time) in Example 1. As indicated in Table 3, at a drying time of 9 minutes, ΔT was 77° C. and a solid content concentration was 74% by weight; and at a drying time of 12 minutes, ΔT was 60° C. and a solid content concentration was 80% by weight. Thus, it was found that ΔT was higher than 70° C. over more than 75% (approximately 90%) of a drying period until the solid content concentration reached 80% by weight.

Further, classification, surface crosslinking, and particle size regulation were carried out in the same manner as in Example 1, to obtain a water absorbent resin 1 for comparison. Physical properties of the water absorbent resin 1 for comparison thus obtained are shown in Table 4.

TABLE 3

| Drying time [min] | Temperature[1] of hot air [° C.] | dew point[1] of hot air [° C.] | Discharge temperature[2] [° C.] | ΔT[3] [° C.] | Solid content concentration [wt %] |
|---|---|---|---|---|---|
| 0 | | | | | 56 |
| 3 | 160 | 60 | 84 | 76 | 57 |
| 6 | 166 | 66 | 92 | 74 | 69 |
| 9 | 172 | 69 | 95 | 77 | 74 |
| 12 | 180 | 66 | 120 | 60 | 80 |
| 15 | 187 | 58 | 147 | 40 | 87 |
| 25 | 190 | 50 | 180 | 10 | 92 |
| 40 | 190 | 42 | 190 | 0 | 94 |
| 60 | 190 | 23 | 190 | 0 | 95 |

[1]Temperature and dew point of hot air blown to particulate hydrogel layer
[2]Temperature of hot air after passing particulate hydrogel layer and through-circulation belt
[3](Temperature of hot air blown to particulate hydrogel layer) – (temperature of hot air after passing particulate hydrogel layer and through-circulation belt)

Comparative Example 2

The particulate hydrogel 1 obtained in Example 1 was dried by using the same drying apparatus as that used in Example 1. The particulate hydrogel 1 was spread into a gel layer of height of 150 mm. The particulate hydrogel 1 was dried while temperature and dew point of hot air were adjusted. The data thus obtained are shown in Table 4. However, surface crosslinking was carried out until the same absorption capacity as that obtained in Example 1 (CRC=30 [g/g]) was attained, by regulating a heat treatment time (also called: reaction time) in Example 1. As indicated in Table 4, at a drying time of 3 minutes, ΔT was 98° C. and a solid content concentration was 65% by weight; and at a drying time of 20 minutes, ΔT was 3° C. and a solid content concentration was 97% by weight. Thus, it was found that ΔT was higher than 70° C. over more than 75% of a drying period until the solid content concentration reached 80% by weight.

Further, classification, surface crosslinking, and particle size regulation were carried out in the same manner as in Example 1, to obtain a water absorbent resin 2 for comparison. Physical properties of the water absorbent resin 2 for comparison thus obtained are shown in Table 6.

TABLE 4

| Drying time [min] | Temperature[1] of hot air [° C.] | dew point[1] of hot air [° C.] | Discharge temperature[2] [° C.] | ΔT[3] [° C.] | Solid content concentration [wt %] |
|---|---|---|---|---|---|
| 0 | | | | | 56 |
| 3 | 178 | 75 | 80 | 98 | 65 |
| 20 | 200 | 30 | 197 | 3 | 97 |

[1]Temperature and dew point of hot air blown to particulate hydrogel layer
[2]Temperature of hot air after passing particulate hydrogel layer and through-circulation belt
[3](Temperature of hot air blown to particulate hydrogel layer) – (temperature of hot air after passing particulate hydrogel layer and through-circulation belt)

Example 3

The particulate hydrogel 1 obtained in Example 1 was dried by using the same drying apparatus as that used in Example 1. The particulate hydrogel 1 was spread into a gel layer of height of 25 mm. The particulate hydrogel 1 was dried by setting a speed of hot air to 0.8 [m/sec] while temperature and dew point of hot air were adjusted. The data thus obtained are shown in Table 5. However, surface crosslinking was carried out until the same absorption capacity as that obtained in Example 1 (CRC=30 [g/g]) was attained, by regulating a heat treatment time (also called: reaction time) in Example 1. As indicated in Table 5, it is noted that substantially throughout the entire drying period until the solid content concentration reached 80% by weight, ΔT was in the range of 20° C. to 70° C. (about 35° C. to 21° C.).

Further, classification, surface crosslinking, and particle size regulation were carried out in the same manner as in Example 1, to obtain a water absorbent resin 3. Physical properties of the water absorbent resin 3 thus obtained are shown in Table 6.

TABLE 5

| Drying time [min] | Temperature[1] of hot air [° C.] | dew point[1] of hot air [° C.] | Discharge temperature[2] [° C.] | ΔT[3] [° C.] | Solid content concentration [wt %] |
|---|---|---|---|---|---|
| 0 | | | | | 56 |
| 4 | 166 | 70 | 131 | 35 | 66 |
| 6 | 170 | 65 | 140 | 30 | 75 |
| 8 | 180 | 62 | 159 | 21 | 84 |
| 20 | 190 | 40 | 190 | 0 | 96 |

[1]Temperature and dew point of hot air blown to particulate hydrogel layer
[2]Temperature of hot air after passing particulate hydrogel layer and through-circulation belt
[3](Temperature of hot air blown to particulate hydrogel layer) – (temperature of hot air after passing particulate hydrogel layer and through-circulation belt)

TABLE 6

| | Example 1 Water absorbent resin 1 | Example 2 Water absorbent resin 2 | Example 3 Water absorbent resin 3 | Comparative Example 1 Water absorbent resin 1 for comparison | Comparative Example 2 Water absorbent resin 2 for comparison |
|---|---|---|---|---|---|
| CRC [g/g] | 30 | 30 | 30 | 30 | 30 |
| AAP (0.7 psi) [g/g] | 24 | 25 | 26 | 19 | 16 |
| SFC [×$10^{-7}$ · $cm^3 \cdot s \cdot g^{-1}$] | 33 | 38 | 40 | 15 | 10 |
| Residual monomers [ppm] | 290 | 320 | 300 | 480 | 430 |

CONCLUSIONS

Physical properties (results) of the water absorbent resins that were subjected to the same pulverization and classification and were subjected to surface crosslinking with the same surface crosslinking agent so as to give absorption capacity (CRC) of 30 [g/g] are shown in Table 4. In spite of the same particulate hydrogels, by applying the drying method of this invention (temperature difference of hot air: 20° C. to 70° C.), reduction in residual monomers disclosed in Patent Literature 1, as well as enhancement of AAP (absorbency against pressure) or SFC (saline flow conductivity) that is not disclosed in Patent Literature 1 were recognized.

Patent Literature 1 (a method of reducing residual monomers by means of hot air having a dew point of 50° C. to 100° C.), Patent Literature 2 (a method of reducing change in physical properties by controlling a direction or temperature of hot air and controlling a dew point to 50° C. or lower), as well as Patent Literatures 3 and 4 have no disclosure on surface crosslinking or on AAP and SFC. Therefore, Patent Literatures 1 to 4 do not suggest any drying method of this invention (temperature difference of hot air being 20° C. to 70° C.) or effects thereby (enhancement of AAP or SFC).

INDUSTRIAL APPLICABILITY

There is provided an efficient drying method for a water absorbent resin, which can maintain or enhance physical properties such as CRC (absorption capacity without load) and Ext (extractables) in high concentration polymerization of a water absorbent resin, cause no coloration, and produce no undried product. Increase in the productivity of water absorbent resin, decrease in cost, decrease in energy used in the production steps (reduction of $CO_2$ emission), and the like, can be attained.

The present patent application is based on Japanese Patent Application No. 2010-050710 filed on Mar. 8, 2010, the entire disclosure of which is incorporated herein by reference.

The invention claimed is:

1. A method for drying a particulate water-containing gel-like crosslinked polymer which comprises polymerizing acrylic acid or partially neutralized salt thereof with a crosslinking agent in an aqueous solution to obtain a particulate water-containing gel-like crosslinked polymer of a partially neutralized salt of polyacrylic acid containing acrylic acid or salt thereof as a main component and having a solid content concentration of 35% to 75% by weight, and drying the particulate water-containing gel-like crosslinked polymer with a through-circulation dryer using hot air having a temperature of 130 to 230° C. and a dew point of 50 to 80° C.,
wherein over 60% or more of a period from a time of introducing the particulate water-containing gel-like crosslinked polymer into a drying zone of the through-circulation dryer to a time of reaching a solid content concentration thereof to 80% by weight, a difference of temperature ($\Delta T$) between a temperature of hot air blown to a particulate hydrogel layer and a temperature measured after the hot air passes through the particulate hydrogel layer is 20 to 70° C.,
wherein the temperature of the particulate water-containing gel-like crosslinked polymer immediately before being introduced into the drying zone is 40 to 70° C., and the dew point of the hot air used in the through-circulation dryer is varied in multiple stages.

2. The method according to claim 1, wherein the difference of temperature between a temperature of hot air blown to the particulate hydrogel layer and a temperature measured after the hot air passes through the particulate hydrogel layer is 30° C. to 60° C.

3. The method according to claim 1, wherein the through-circulation dryer is a through-circulation band dryer.

4. The method according to claim 3, wherein the through-circulation band dryer has a plurality of chambers.

5. The method according to claim 1, wherein the temperature of the hot air used in the through-circulation dryer is varied in multiple stages.

6. The method according to claim 1, wherein over 70% or more of the period until the solid content concentration reaches 80% by weight, the dew point of used hot air is 50 to 80° C.

7. The method according to claim 1, wherein over 90% or more of the period until the solid content concentration reaches 80% by weight, the dew point of used hot air is 50 to 80° C. and/or the difference of temperature ($\Delta T$) is 20 to 70° C.

8. A method for producing a water absorbent resin, which comprises the method set forth in claim 1, and further comprising surface crosslinking the particulate water-containing gel-like crosslinked polymer after the drying.

9. The method according to claim 2, wherein the through-circulation dryer is a through-circulation band dryer.

10. The method according to claim 9, wherein the through-circulation band dryer has a plurality of chambers.

11. The method according to claim 2, wherein the temperature of the hot air used in the through-circulation dryer is varied in multiple stages.

12. The method according to claim 3, wherein the temperature of the hot air used in the through-circulation dryer is varied in multiple stages.

13. The method according to claim 4, wherein the temperature of the hot air used in the through-circulation dryer is varied in multiple stages.

* * * * *